(12) United States Patent
Li et al.

(10) Patent No.: US 7,632,863 B2
(45) Date of Patent: Dec. 15, 2009

(54) 3,4,5,4'-TETRAMETHOXYL-α,β-DIPHENYLETHANE-3'-O-SODIUM SULPHATE AND ITS USE

(75) Inventors: Yiping Li, Taizhou (CN); Ning Li, Taizhou (CN); Danping Zhou, Taizhou (CN); Lizuan Chen, Taizhou (CN)

(73) Assignee: The Jian Cell Biomedical Research Co., Ltd., Taizhou (CN)

( * ) Notice: Subject to any disclaimer, the term of this patent is extended or adjusted under 35 U.S.C. 154(b) by 0 days.

(21) Appl. No.: 12/023,778

(22) Filed: Jan. 31, 2008

(65) Prior Publication Data

US 2008/0234369 A1    Sep. 25, 2008

(30) Foreign Application Priority Data

Feb. 1, 2007    (CN) .................. 2007 1 0063472

(51) Int. Cl.
*A01N 55/02*    (2006.01)
(52) U.S. Cl. ................... 514/492; 514/517; 558/33
(58) Field of Classification Search .................. 514/146
See application file for complete search history.

(56) References Cited

OTHER PUBLICATIONS

Nandy, Partha, Quantitative Structure-Activity Relationship Analysis of Combretastatisn: a Class of Novel Antimitotic Agents, Pharmaceutical Research, vol. 8, No. 6, 1991.*

* cited by examiner

*Primary Examiner*—Sikarl A Witherspoon
*Assistant Examiner*—Chukwuma O Nwaonicha
(74) *Attorney, Agent, or Firm*—Occhiuti Rohlicek & Tsao LLP

(57) ABSTRACT

This invention relates to a compound of formula (I), 3,4,5,4'-tetramethoxyl-α,β-diphenylethane-3'-O-sodium sulphate, and its use in the preparation of antineoplastic pharmaceutical.

(I)

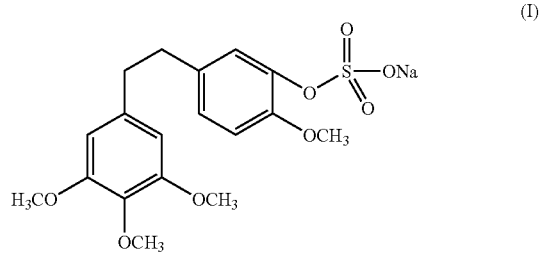

13 Claims, No Drawings

3,4,5,4'-TETRAMETHOXYL-α,β-DIPHENYLETHANE-3'-O-SODIUM SULPHATE AND ITS USE

CROSS-REFERENCE TO RELATED APPLICATIONS

This application claims the benefit of Chinese Application Serial No. 200710063472.1, filed on Feb. 1, 2007. The content of the foregoing application is hereby incorporated by reference in its entirety.

FIELD OF INVENTION

This invention relates to 3,4,5,4'-tetramethoxyl-α,β-diphenylethane-3'-O-sodium sulphate and its use.

BACKGROUND OF INVENTION

Cancer is a disease that seriously jeopardizes the health of human beings. Around the globe, about 6 million people die of cancer every year, with another 10 million on the brink of death. According to the estimate of the World Health Organization, in the $21^{st}$ century, cancer will become the "number one killer" of mankind. The national retrospective investigation on the causes of death showed that in the past two decades, the morbidity and death rate of cancer in China have been on the rise year by year. Out of every five people died of disease, one was of cancer; for every 200 families, one suffered the pain of having a family member with cancer.

In the past several decades, many ways of treating cancer became available, mainly including surgery, radiotherapy, chemotherapy, hormonotherapy, gene therapy, and immunotherapy, among which surgery, radiotherapy and chemotherapy have became the major means. Chemotherapy refers to treating cancer with chemical medication. It is the field of the most rapid development in the diagnosis and treatment of cancer. A great number of new medicines aiming at different targets are ready for clinical application, and developments in research in mechanism of drug action and pharmacokinetics have made the clinical administration routes and means more fitting for killing tumor cells while protecting the normal tissues.

At present, pharmaceutical for chemotherapy mainly includes: pharmaceutical that affects the biosynthesis of nucleic acid, e.g. fluorouracil, 6-oxypurine, amethopterin, cytarabine, hydroxyurea; pharmaceutical that directly destroys DNA and prevents its reproduction, e.g. alkylating agents; antineoplastic antibiotics, e.g. Cisplatin and Carboplatin; pharmaceutical that interferes with the transcription and prevents the synthesis of RNA, e.g. actinomycin D, adriamycin, and other transcription restraining antibiotics; pharmaceutical that affects the synthesis of protein, e.g. catharanthines, podophyllotoxins, harringtonine, asparaginase; hormones, e.g. adrenal cortical hormone, estrogen, androgen, tamoxifen, aminoglutethimide. The existing chemotherapies and radiotherapies that are commonly used in treating cancer may cause serious toxic and other side effects that are adverse to the human body.

The property of interfering the polymerization or depolymerizaion of microtubulin of many natural medicines is regarded as having antineoplastic activity. Such medicines include vincristine, taxanes, and macrolide antineoplastic drugs. Microtubules play an important role in cell division, and the development of microtubulin binding factors is based on their capability of interfering cell proliferation. The depolymerizing factor of microtubulin, such as colchicine and vincristine, has the antimitotic effect, causing the tumor vessels to close. However, such effect of closing the tumor vessels only occurs when the dosage approaches the MTD (maximum tolerated dose). Endostatin, the latest discovered inhibiting factor of vasculogenesis, has the inhibiting effect on new vasculogenesis, but has no obvious effect on existing vessels or obvious target effect on tumor vessels.

A new type of microtubulin depolymerizing factor discovered in recent years can solve this problem by closing the vessels with dosage well below the MTD (Expert Opin Investig Drugs. 2004 September; 13 (9) 1171-82). In 2005, Loïc Vincent et al. mentioned a new type of microtubulin depolymerizing factor with similar property destroying microtubulin skeleton as vascular targeting factors (VTAs). Literature data shows that VTAs can selectively induce the decay of tumor vessels, partly through the VE-cadherin signal channel. This kind of microtubulin depolymerizing factor selectively destroys tumor vessels and prevent new vasculogenesis in the tumor while having no influence on the normal vascular system. At the same time, it can inhibit the polymerization of microtubulin, selectively cause tumor vessel function disorder and structural damage, and induce the apoptosis of vessel endothelial cells, playing its role of killing tumor cells or inhibiting tumor metastasis by making tumor cells lose the support of nutrition and oxygen.

In 2005, Gillian M. Tozer et al. reported in an influential journal, Nature Rev Cancer, that this kind of compound not only affects the proliferation of endothelial cells, but also influences their migration, quickly changing the pattern of endothelial cells, causing their apoptosis, and breaking their connections, so as to immediately cause the tumor vessel function disorder and structural damage. As the normal vessels are generally supported by smooth muscle cells, this kind of compound only affects the vessels without such support and has no influence on vessels supported by smooth muscle cells, it can quickly and selectively cause the tumor vessel function disorder and structural damage, thus affecting the tumor cells selectively (Nat Rev Cancer. 2005 June; 5(6) 423-35, J. Clin. Invest., Nov. 1, 2005; 115(11): 2992-3006). 2992-3006). At present, this type of medication is regarded as one of the most promising antineoplastic medicines.

Now Combretastatin A-4 is the only medicine of this kind that is under research overseas, whose research has entered the clinical stage. Through double bond connection, the most effective configuration in the stilbene units of Combretastatin to destroy tumor vessels is its cis-configuration, and the stilbene compound of trans-configuration has no inhibiting effect on tumors. It is very easy for reactions such as isomerization to take place due to the existence of cis, trans isomerism. The trans-configuration not only lacks efficacy, but also brings certain toxic side effects at the same time (for Combretastatin A-4, LD50 is 500 mg/kg), resulting in great difficulty in the preservation and actual application of Combretastatin A-4.

3,4,5,4'-tetramethoxyl-α,β-diphenylethane-3'-O-sodium sulphate of this invention is a synthesized compound, its structural formula being the following formula (I):

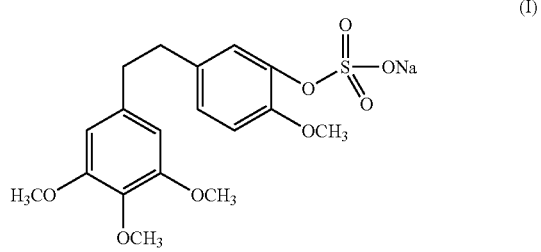

It is an entirely new chemical substance as well as a tumor vessel inhibitor of entirely new structure innovated and developed by the inventor. Unlike Combretastatin A-4, the two benzene rings are connected by single bond, which results in the differences in structure, conformation, bonding force, and trans effect between 3,4,5,4'-tetramethoxyl-α,β-diphenylethane-3'-O-sodium sulphate and Combretastatin A-4, greatly increasing the stability of compound (Light may isomerize Combretastatin A-4 to trans-configuration, so it should be kept out of light) and the effect over microtubulin.

3,4,5,4'-tetramethoxyl-α,β-diphenylethane-3'-O-sodium sulphate has good water solubility. By directional targeting, it pointedly affects tumor vessels without affecting non-tumor vessel, showing greater advantage over traditional chemotherapeutics that directly inhibit the growth of tumor cells as well as overcoming the limitations in toxic side effects and drug tolerance of traditional antineoplastic drugs. Antineoplastic research of it showed that 3,4,5,4'-tetramethoxyl-α,β-diphenylethane-3'-O-sodium sulphate not only can kill tumor cells, but according to joint administration experiment, it also remarkably enhances the efficacy of chemotherapeutics.

SUMMARY OF INVENTION

One object of this invention is to provide a compound of formula (I), its chemical name being 3,4,5,4'-tetramethoxyl-α,β-diphenylethane-3'-O-sodium sulphate.

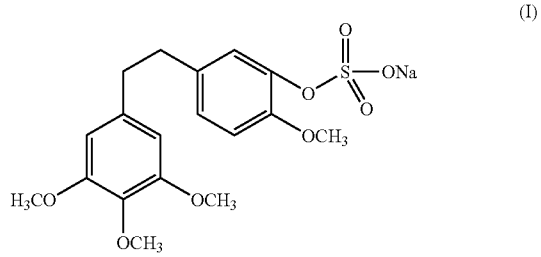

In formula (I), Na can be replaced by H, $NH_4$, K, other metals, ammonium salts, or organic amine.

Another object of this invention is to provide a pharmaceutical composition comprising the compound of formula (I). Using the compound of formula (I) as the effective ingredient, and adding pharmaceutically acceptable accessories, the pharmaceutical composition of this invention can be obtained.

A third object of this invention is to provide a use of compound (I) or the pharmaceutical composition comprising compound (I) in preparing pharmaceutical for treating tumors.

A fourth object of this invention is to provide a method of treatment of tumors by administering to a subject in need of such treatment a compound of formula (I) or a compound of formula (I) in combination with other antitumor agents.

Tumors referred to in this invention may be solid tumors such as sarcomas and cancers (for instance, fibrosarcoma, myxosarcoma, liposarcoma, chondrosarcoma, osteogenic sarcoma, notochordoma, hemangiosarcoma, endotheliosarcoma, lymphangiosarcoma, lymphangioendotheliosarcoma, synovial bursa, mesothelioma, Ewing's tumor, leiomyosarcoma, rhabdomyosarcoma, carcinoma of colon, carcinoma of pancreas, breast cancer, oophoroma, prostatic carcinoma, squamous carcinoma, basaloma, adenocarcinoma, syringocarcinoma, sebaceous carcinoma, papillary carcinoma, papillary adenocarcinoma, cystadenocarcinoma, encephaloid carcinoma, bronchiolar carcinoma, renal cell carcinoma, liver neoplasm, cholangiocarcinoma, choriocarcinoma, seminoma, embryonal carcinoma, Wilms' tumor, cervical carcinoma, uterine cancer, carcinoma of testis, lung cancer, small cell carcinoma of lung, carcinoma of urinary bladder, epithelial cancer, glioma, astrocytic glioma, acoustic tumor, oligodendroglioma, neurinoma, meningeoma, melanoma, neuroblastoma and retinoblastoma), or hematic tumors such as leukemia (for instance, acute leukocythemia, acute lymphoblastic leukemia, acute myeloblastic leukemia, acute myelogenous leukemia, acute promyelocytic leukemia, acute myelomonocytic leukemia, acute monocytic leukemia, acute erythroleukemia, chronic leukemia, chronic myeloblastic leukemia, chronic lymphoblastic leukemia), polycythemia vera, lymphoma (Hodgkin's disease, non-Hodgkin's disease), Waldenstrom's macroglobulinemia, heavy chain disease. And sarcoma, liver cancer, lung cancer, melanoma, leukemia, esophageal cancer, and adenocarcinoma of stomach are selectively preferable.

Researches showed that 3,4,5,4'-tetramethoxyl-α,β-diphenylethane-3'-O-sodium sulphate can inhibit the polymerization of microtubulin, selectively cause tumor vessel function disorder and structural damage, and induce the apoptosis of vessel endothelial cells, playing its role of killing tumor cells or inhibiting tumor metastasis by making tumor cells lose the support of nutrition and oxygen.

3,4,5,4'-tetramethoxyl-α,β-diphenylethane-3'-O-sodium sulphate may also be jointly used with other therapies such as chemotherapy, surgery, radiotherapy, immunotherapy, antivasculogenesis therapy or gene therapy to remarkably enhance the curative effect on tumors. Preferably, the said other therapy is the chemotherapy using antineoplastic drugs. More preferably, the said other therapy is the one using cytotoxin and anti-multiplication and vasculogenesis inhibiting drugs, the preferred medicines including Cisplatin, fluorouracil, adriamycin, leuleran, melphalan, taxol, irinotecan CPT-11, Avastin, ZD6126 (N-acetylcochinol-O-phosphate, vascular endothelial-cadherin antibodies anti-E-cadherin (BV13) or against VE-cadherin (E4G10), etc.

In the experiment of its joint administration with DDP on S180 tumor model, 3,4,5,4'-tetramethoxyl-α,β-diphenylethane-3'-O-sodium sulphate showed excellent coordinating effect in combination with DDP in inhibiting S180 tumors.

By using 3,4,5,4'-tetramethoxyl-α,β-diphenylethane-3'-O-sodium sulphate as the effective ingredient, adding pharmaceutically acceptable accessories, and using the common method of this field, a pharmaceutical composition of this invention can be prepared. The dosage forms of the pharmaceutical composition can be: oral administration form, such as tablet, capsule (including hard capsule, soft capsule, enteric-coated capsule and microcapsule), powder, granules and syrups; non-oral administration form, such as injection, lyophilization, suppositories, pill, gelata and patch. Besides these common forms, the orally taken speed-release preparation (such as tablet, granules) and the orally or non-orally taken sustained-release preparation (such as tablet, granules, refined granules, pill, capsule, syrup, stable suspension, solution) can also be used in current invention, and preparations thereof are available by common methods. The preparation in current invention can be coated or non-coated according to the need. The injection form and the orally taken form of preparation of 3,4,5,4'-tetramethoxyl-α,β-diphenylethane-3'-O-sodium sulphate are preferred in this invention.

The medicated accessories in this invention include those for solid preparation, such as excipient, lubricant, cohesives, disintegrant, stabilizer, blowing agent, coating agent, etc; or those for semisolid preparation and liquid preparation, such as solvent, solubilizing agent, suspending agent, isotonizing agent, buffer, emollient, emulsifier, etc. In addition, other pharmaceutical additives, such as preservative, antioxidant, colorant, edulcorant, correctant, etc. can also be used if necessary.

The following embodiments are presented to describe the invention without bringing any limitation to the scope of protection of this invention.

DETAILED DESCRIPTION OF INVENTION

Preparation of 3,4,5,4'-tetramethoxyl-α,β-diphenylethane-3'-O-sodium sulphate

EXAMPLE ONE

Preparation of 3,4,5,4'-tetramethoxyl-α,β-diphenylethane-3'-O-sodium sulphate 3,4,5,4'-tetramethoxyl-α,β-diphenylethane-3'-O-sodium sulphate used in this invention is provided by Zhejiang Cell Biomedical Research CO., LTD., and other test materials are all purchased commercially, unless indicated otherwise.

The detailed process for the preparation of 3,4,5,4'-tetramethoxyl-α,β-diphenylethane-3'-O-sodium sulphate is as follows:

1. The preparation of 3,4,5-trimethoxybenzylalcohol 3,4,5-trimethoxybenzaldehyde (15 g, 76.45 mmol) and anhydrous alcohol (200 ml) were placed in a 250 ml three-necked flask, and were dissolved at 40° C. Sodium borohydride (1.48 g, 38.23 mmol) was added to the solution. The resulting mixture was heated to reflux for 45 minutes, and monitored by TLC. When the reaction is completed, cooling it to room temperature, deionized water (10 ml, 555.8 mol) was added to quench the reaction. After suction filtering, the filter residue was washed by anhydrous alcohol (20 ml), the combined filtrate was concentrated in rotatory evaporator to dry, dichlormethane (100 ml) was added to dissolve the crude product. The organic layer was washed with sodium hydroxide solution (50 ml) twice and with deionized water (50 ml) twice, and a proper amount of anhydrous magnesium sulfate was added to dry it overnight. After filtering, washing the filter residue with dichlormethane (20 ml). The combined filtrate was concentrated in a rotatory evaporator to afford 3,4,5-trimethoxyl benzyl alcohol, 14.05 g of colorless oily product, yield: 92.72%

The product does not need to be further purified for following reaction. If pure product is wanted, it can be vacuum distilled for the fraction of distillate of BP 216-218° C./12 mmHg.

2. The preparation of 3,4,5-trimethoxyl benzyl bromide

Dissolving 3,4,5-trimethoxyl benzyl alcohol (14.05 g, 70.89 mmol) in dichlormethane (100 ml) in a 250 ml three-necked flask; phosphorus tribromide (6.73 ml, 70.89 mmol) in dichlormethane (25 ml) was added dropwise and allowed to react at room temperature for 50 minutes, cooling in ice bath, slowly adding deionized water (18 ml, 1.0 mol) dropwise to quench the reaction, washing with deionized water (100 ml) twice, drying with anhydrous magnesium sulfate, filtering, washing the filter residue with dichlormethane (20 ml), the combined organic layer was concentrated in rotatory evaporator to dry, and was further dried under vacuum to afford 3,4,5-trimethoxyl benzyl bromide (16.05 g of faint yellow solid), yield 84.44%.

The product does not need to be further purified for following reaction. If pure product is wanted, it can be recrystallized to get the white lamellar crystal with a 1:3 mixture of ethyl acetate and n-hexane.

3. The preparation of 3,4,5-trimethoxyl benzyl triphenylphosphine bromide

Dissolving 3,4,5-trimethoxyl benzyl bromide (16.05 g, 61.47 mmol) in toluene (150 ml) in a 250 ml three-necked flask, adding triphenylphosphine (16.12 g, 61.47 mmol) and dissolving immediately. The reaction mixture was heated to reflux for 1 hour, white solid was separated, then cooling to room temperature, suction filtering, the filter cake was washed with toluene (30 ml). After vacuum drying, 3,4,5-trimethoxyl benzyl triphenylphosphine bromide (27.81 g of white powder solid) was isolated, yield: 86.44%.

The product does not need to be further purified for following reaction. If pure product is needed, it can be washed with acetone to get white powder solid.

4. The Preparation of Isovanillin Protected by Benzyl Group

Adding isovanillin (15 g, 98.59 mmol) to anhydrous alcohol (200 ml) in a 250 ml three-necked flask, heating to dissolve at 40° C., adding potassium carbonate (9 g, 65.07 mmol), adding benzylchloride (15 ml, 130.13 mmol) under stirring. The resulting mixture was heated to reflux for 1 hour; After the completion of the reaction (monitored by TLC), cooling it down to 50° C., filtering while hot, cooling the filtrate in refrigeratory overnight, crystal was precipitated, suction filtering, and washing the filter cake with toluene (30 ml). After vacuum drying, the benzyl group protecting isovanillin (white acicular crystal, 19.72 g) was isolated, yield: 82.56%.

The product does not need to be further purified for following reaction. If pure product is needed, it can be recrystallized by absolute alcohol to get white styloid solid.

5. The preparation of (Z) and (E)-3,4,5-trimethoxyl-3'-benzyloxy-4'-methoxystilbene Adding 3,4,5-trimethoxyl benzyl triphenylphosphine bromide (20.00 g, 38.21 mmol) and tetrahydrofuran (150 ml) in a 250 ml three-necked flask, stirring the suspension, dissolving isovanillin protected by benzyl group (10.00 g, 41.27 mmol) in tetrahydrofuran (70 ml), and adding it to a dropping funnel (100 ml); adding solid potassium t-butoxide (7.46 g, 66.49 mmol) to the reaction flask, when the reaction system turning to sanguine, stirring for 5 minutes at room temperature, slowly adding the solution of isovanillin protected by benzyl group dropwise, and stirring for 20 minutes at room temperature again; After the completion of the reaction (monitored by TLC), the reaction mixture was transferred into a 500 ml separating funnel, adding deionized water (140 ml), the solution being stratified, extracting with diethyl ether (300 ml) twice, collecting the ether layer, drying with anhydrous magnesium sulfate, filtering, and the filter cake was washed with dry ether (50 ml); concentrating the filtrate in rotatory evaporater to dry to get oily product (25 g); adding absolute alcohol to solidify it, a faint yellow solid (12.50 g) was obtained by suction filtering, yield: 80.48%.

6. The recrystallization of (Z) and (E)-3,4,5-trimethoxyl-3'-benzyloxy-4'-methoxystilbene Adding cis/trans isomer (12.50 g, 30.75 mmol) and anhydrous alcohol (20 ml) in a 50 ml round bottom flask, heating till some solid is dissolved, stirring at room temperature, suction filtering, the filter cake was washed with dry ether (10 ml), and drying by Infrared lamp to get pure cis/trans isomer (9.27 g) in faint yellow powder, yield: 74.16%

7. The preparation of 3,4,5-trimethoxyl-3'-hydroxy-4'-methoxy-α,β-diphenylethane Dissolving pure (Z) and (E)-3,4,5-trimethoxyl-3'-benzyloxy-4'-methoxystilbene (5.14 g, 12.56 mmol) in the mixture of ethyl acetate (100 ml) and absolute alcohol (60 ml) in a 250 ml three-necked flask, the solution being faint yellow, adding 5% Pd—C (0.5 g), stirring while passing hydrogen into the mixture, stirring for 1 hour at room temperature, filtering. After filtering the colorless filtrate was concentrated in rotatory evaporater to dry to obtain a oily product (4.05 g), the crude product of Erianin, yield: 100%.

8. The purification of 3,4,5-trimethoxyl-3'-hydroxy-4'-methoxy-α,β-diphenylethane Dissolving the crude product of 3,4,5-trimethoxyl-3'-hydroxy-4'-methoxy-α,β-diphenylethane (4.05 g, 12.72 mmol) in anhydrous alcohol (20 ml) in a 50 ml round bottom flask, filtering the insoluble substance (if any), and leaving it in stillness for white crystal to be separated at room temperature, then standing overnight. When the solvent is completely volatilized, a great quantity of white crystal is separated. After suction filtering, the filter cake was washed with alcohol to afford the white crystal (3.56 g), yield: 100%.

9. Salt-forming Reaction

Adding 3,4,5-trimethoxyl-3'-hydroxy-4'-methoxyl-dihydrostilbene (10 mmol) and N,N-dimethyl aniline (75 mmol) in a 250 ml round bottom flask, adding $CH_2Cl_2$ of equal volume to N,N-dimethyl aniline, stirring in ice-salt bath (−5~−10° C.), and adding dropwise chlorosulfonic acid (12.5 mmol); then continuing to stir for 1 hour in brine bath, removing the brine bath, stirring for 24 hours at room temperature, adjusting the PH value of reaction liquid to 10 with NaOH (10 mol/L) under stirring. Then the resulting mixture was cooled in refrigerator. After filtration, the filtrating residue was washed with dry ether, dissolving the solid product in methanol and it was purified by column chromatography after drying, and evaporating the solvent to get a white solid (hydroscopic), 3,4,5,4'-tetramethoxyl-α,β-diphenylethane-3'-O-sodium sulphate.

Characterization by spectra data:

$^1$H NMR ($D_2O$): δ: 2.79 (d, 1H, J=13.7 Hz, H-1α'), 2.80 (d, 1H, J=13.7 Hz, H-1α), 3.67 (s, 3H, 4'=OCH$_3$), 3.74 (s, 6H, 3,5-OCH$_3$), 3.75 (s, 3H, 4-OCH$_3$), 6.55 (s, 2H, H-2.6), 6.58 (d, 1H, J=8.36 Hz, H-5'), 6.85 (d, 1H, J=8.36 Hz, H-6'), 7.33 (d, 1H, J=1.8 Hz, H-2'). $^{13}$C NMR ($D_2O$): δ152.27, 148.05, 148.00, 143.35, 139.54, 135.14, 134.71, 122.32, 120.63, 114.33, 108.03, 106.21, 61.01, 56.30, 56.09, 37.590, 36.70; IR(KBr): u3539s, 3433m, 3001w, 2939m, 2841m, 1589s, 1508s, 1446m, 1422m, 1330m, 1262m, 1242s, 1174m, 1131s, 1014m, 619m, cm$^{-1}$. MS (ESI): m/z: 398.427 (M+). Calc. 421.46 for $C_{18}H_{22}O_8SNa$.

Safety Evaluation of 3,4,5,4'-tetramethoxyl-α,β-diphenylethane-3'-O-sodium sulphate

EXAMPLE TWO

The LD50 determination of 3,4,5,4'-tetramethoxyl-α,β-diphenylethane-3'-O-sodium sulphate 1. Experimental animal: KunMing (KM) mice, provided by Shanghai Slac Laboratory Animal Co., Ltd., half and half of female and male, 6 groups, ten in each group, marked by bitter acid.
2. Preparation of 3,4,5,4'-tetramethoxyl-α,β-diphenylethane-3'-O-sodium sulphate (AS) solution: AS provided by Zhejiang Cell Biomedical Research Co., Ltd., preparing by the process in Example One. Preparing medical solution of equal ratio: dissolving with 0.9% NaCl to prepare the medical solution with the concentration of 336 mg/7 ml, 316.96 mg/7 ml, 299.32 mg/7 ml, 282.52 mg/7 ml, 266.84 mg/7 ml, 252 mg/7 ml.
3. Dosage for administration: with 0.5 ml/20 g bottom up.
4. Means of administration: tail vein injection
5. Experimental method: observing at 0.25 h, 0.5 h, 1 h, 2 h, 4 h, 24 h respectively after administration; then observing once every day 14 days; putting the mice still alive to death on the 15th day and recording the death rate.

TABLE 1

Dosage-Death rate data sheet (n = 3)

| Dosage (mg/kg) | Deaths | | | | | | | | | | Death rate in total % | | |
|---|---|---|---|---|---|---|---|---|---|---|---|---|---|
| | hours | | days | | | | | | | | | | |
| | 0-4 | | 1 | | 2 | | 3 | | 4 | | | | |
| | ♂ | ♀ | ♂ | ♀ | ♂ | ♀ | ♂ | ♀ | ♂ | ♀ | ♂ | ♀ | Total |
| 1200 | 5 | 2 | 0 | 0 | 0 | 0 | 0 | 0 | 0 | 0 | 100 | 40 | 70 |
| 1132 | 3 | 3 | 0 | 0 | 0 | 0 | 0 | 0 | 0 | 0 | 60 | 60 | 60 |
| 1069 | 4 | 4 | 0 | 0 | 0 | 0 | 0 | 0 | 0 | 0 | 80 | 80 | 80 |
| 1009 | 3 | 1 | 0 | 0 | 0 | 0 | 0 | 0 | 0 | 0 | 60 | 20 | 40 |
| 953 | 0 | 0 | 0 | 0 | 0 | 0 | 0 | 0 | 0 | 0 | 0 | 0 | 0 |
| 900 | 0 | 0 | 0 | 0 | 0 | 0 | 0 | 0 | 0 | 0 | 0 | 0 | 0 |

Note:
n is the times repeated of the experiment

Experiment Result

AS $LD_{50}$=1077 mg/kg, $LD_{50}$ (Feiller correction) 95% confidence interval: 1033 mg/kg≦LD50≦1134.7 mg/kg It means that the toxicity of 3,4,5,4'-tetramethoxyl-α,β-diphenylethane-3'-O-sodium sulphate is very low, and is very safe in clinical application.

The Pharmacodynamics Experiment for 3,4,5,4'-tetramethoxyl-α,β-diphenylethane-3'-O-sodium sulphate in S180 Tumor Model

EXAMPLE THREE

Effect of 3,4,5,4'-tetramethoxyl-α,β-diphenylethane-3'-O-sodium sulphate on S180 Tumors 1. Experiment Sample
(1) Sample: 3,4,5,4'-tetramethoxyl-α,β-diphenylethane-3'-O-sodium sulphate (AS) provided by Zhejiang Cell Biomedical Research Co., Ltd., and prepared by the process in Example One. Dissolved by physiological saline for the concentration needed.
(2) Control product: Cyclophosphamide for injection (CTX), Jiangsu Hengrui Pharmaceutical Inc. Co. Batch No.: 04123021 Dissolved by physiological saline for preparation.
2. Animals and Tumor Cell Strains
(1) KM mouse bearing S180 sarcoma.
(2) 50 KM mice, female, weighting 18-22 g, provided by Zhejing College of Traditional Chinese Medicine.
3. Experimental Method
(1) Drawing ascites under aseptic condition from mouse bearing S180 sarcoma, diluting with physiologic saline 1:3, giving subcutaneous inoculation in the armpit of the right forelimb of the KM mice with 0.2 ml each; dividing the mice into 5 groups randomly the next day, 10 in each group.
(2) Administering drug to the mice by weight the third day of inoculation, intravenous administration 0.5 ml/20 g for 11 days, by weight, and putting them to death on the 11th day after inoculation, weighing the tumor and calculating the rate of tumor inhibition.
(3) dosage (mg/kg/d) and means of administration:
AS: 50 mg/kg, tail vein injection
AS: 100 mg/kg, tail vein injection
AS: 200 mg/kg, tail vein injection
CTX: 30 mg/kg, tail vein injection
Setting up another blank control group, tail vein injection of 0.9% NaCl 0.5 ml.
(4) Judging the result with the following formula:

$$\text{Tumor inhibiting rate} = \frac{\text{Tumor weight of control group} - \text{tumor weight of administration group}}{\text{Tumor weight of control group}} \times 100\%$$

4. Experiment Result
During the experiment, no death occurred in any group. The experiment result of inhibiting S180 sarcoma with AS administration is shown in Table 1.

Result Analysis 3,4,5,4'-tetramethoxyl-α,β-diphenylethane-3'-O-sodium sulphate has excellent inhibitory effect on S180 tumors.

The Pharmacodynamics Experiment for the Joint Administration of 3,4,5,4'-tetramethoxyl-α,β-diphenylethane-3'-O-sodium sulphate and DDP in S180 Tumor Model

EXAMPLE FOUR

Effect of the Joint Administration of 3,4,5,4'-tetramethoxyl-α,β-diphenylethane-3'-O-sodium sulphate and DDP on S180 Tumors I. Content of Experiment
1. Experiment Sample
(1) Sample: 3,4,5,4'-tetramethoxyl-α,β-diphenylethane-3'-O-sodium sulphate (AS) provided by Zhejiang Cell Biomedical Research Co., Ltd., and prepared by the process in Example One. Dissolved by physiological saline for the concentration needed.
(2) Cisplatin: Cisplatin for injection (DDP), Qilu Pharmaceutical Co., Ltd. Batch No.: 5120282DC. Dissolved by physiological saline for preparation.
(3) Control product: Cyclophosphamide for injection (CTX), Jiangsu Hengrui Pharmaceutical Inc. Co. Batch No.: 04123021 Dissolved by physiological saline for preparation.
2. Animals and Tumor Cell Strains
(1) KM mouse bearing S180 sarcoma.
(2) 70 KM mice, female, weighting 18-22 g, provided by Zhejing College of Traditional Chinese Medicine.
3. Experimental Method
(1) Drawing ascites under aseptic condition from mouse bearing S180 sarcoma, diluting with physiologic saline 1:3, giving subcutaneous inoculation in the armpit of the right forelimb of the KM mice with 0.2 ml each; dividing the mice into 7 groups randomly the next day, 10 in each group.
(2) Administering drug to the mice by weight the third day of inoculation, intravenous administration 0.5 ml/20 g for 11 days, by weight, and putting them to death on the 11th day after inoculation, weighing the tumor and calculating the rate of tumor inhibition.
(3) dosage (mg/kg/d) and means of administration:
AS: 50 mg/kg, tail vein injection
AS: 100 mg/kg, tail vein injection
AS: 200 mg/kg, tail vein injection
DDP: 1 mg/kg, tail vein injection
AS+DDP: 50 mg/kg+1 mg/kg, tail vein injection

TABLE 1

Experiment result of inhibiting tumors in mice bearing S180 sarcoma with AS administration

| Sample | Dosage (mg/kg) | Means of administration | Number of animal | 0 d weight (g) | 11 d weight without tumor (g) | Tumor weight (g) | Tumor inhibiting rate % |
|---|---|---|---|---|---|---|---|
| AS | 50 | i.v. | 10/10 | 21.06 ± 0.82 | 25.89 ± 3.32 | 1.63 ± 1.43 | 44% |
| AS | 100 | i.v. | 10/10 | 20.46 ± 1.03 | 28.42 ± 4.13 | 2.07 ± 1.03 | 29% |
| AS | 200 | i.v. | 10/10 | 20.45 ± 0.86 | 27.10 ± 2.44 | 1.34 ± 0.53 | 54% |
| CTX | 1 | i.v. | 10/10 | 21.18 ± 0.64 | 26.28 ± 1.72 | 0.90 ± 0.26 | 69% |
| Control | 0.9% NaCl | i.v. | 10/10 | 20.60 ± 1.43 | 27.14 ± 3.72 | 2.93 ± 0.92 | |

CTX: 30 mg/kg, tail vein injection
DDP: 1 mg/kg, tail vein injection
Setting up another blank control group, tail vein injection of 0.9% NaCl 0.5 ml.
(4) Judging the result with the following formula:

$$\text{Tumor inhibiting rate} = \frac{\text{Tumor weight of control group} - \text{tumor weight of administration group}}{\text{Tumor weight of control group}} \times 100\%$$

II. Experiment Result

During the experiment, no death occurred in any group. The experiment results of inhibiting S180 sarcoma with AS administration as well as joint administration of AS and DDP are shown in Table 2.

TABLE 2

Experiment results of inhibiting tumors in S180 sarcoma-bearing mice with the joint administration of AS and DDP

| Sample | Dosage (mg/kg) | Means of administration | Number of animal | 0 d weight (g) | 11 d weight without tumor (g) | Tumor weight (g) | Tumor inhibiting rate % |
|---|---|---|---|---|---|---|---|
| AS | 50 | i.v. | 10/10 | 21.06 ± 0.82 | 25.89 ± 3.32 | 1.63 ± 1.43 | 44% |
| AS | 100 | i.v. | 10/10 | 20.46 ± 1.03 | 28.42 ± 4.13 | 2.07 ± 1.03 | 29% |
| AS | 200 | i.v. | 10/10 | 20.45 ± 0.86 | 27.10 ± 2.44 | 1.34 ± 0.53 | 54% |
| DDP | 30 | i.v. | 10/10 | 20.84 ± 1.94 | 25.38 ± 3.23 | 0.88 ± 0.50 | 70% |
| AS + DDP | 50 ± 1 | i.v. | 10/10 | 21.27 ± 1.48 | 26.27 ± 1.49 | 1.06 ± 0.41 | 64% |
| CTX | 1 | i.v. | 10/10 | 21.18 ± 0.64 | 26.28 ± 1.72 | 0.90 ± 0.26 | 69% |
| Control | 0.9% NaCl | i.v. | 10/10 | 20.60 ± 1.43 | 27.14 ± 3.72 | 2.93 ± 0.92 | |

III. Result Analysis:

The joint administration of 3,4,5,4'-tetramethoxyl-α,β-diphenylethane-3'-O-sodium sulphate and DDP showed a fine coordinating effect in inhibiting S180 tumors.

The Tumor Inhibiting Rate Experiment for the Joint Administration of 3,4,5,4'-tetramethoxyl-α,β-diphenylethane-3'-O-sodium sulphate and DDP in Murine Model of Lewis Lung Cancer

EXAMPLE FIVE

Tumor Inhibiting Effect of the Joint Administration of 3,4,5,4'-tetramethoxyl-α,β-diphenylethane-3'-O-sodium sulphate and DDP on Murine Model of Lewis Lung Cancer I. Content of Experiment 1. Experiment Sample (1) Sample: 3,4,5,4'-tetramethoxyl-α,β-diphenylethane-3'-O-sodium sulphate (AS), raw material medicine, provided by Zhejiang Cell Biomedical Research Co., Ltd., and prepared by the process in Example One. Batch No.: 061025. Dissolved by physiological saline for the concentration needed.

(2) Cisplatin: Cisplatin for injection (DDP), Qilu Pharmaceutical Co., Ltd. Batch No.: 5120282DC; Dissolved by physiological saline for preparation (3) Control product: Cyclophosphamide for injection (CTX), Jiangsu Hengrui Pharmaceutical Inc. Co. Batch No.: 04123021. Dissolved by physiological saline for preparation.

2. Animals and Tumor Cell Strains (1) C57BL/6J mouse bearing Lewis lung cancer (2) 70 C57BL/6J mice, female, weighing 17-21 g. Provided by the animal house of Zhejiang Cell Biomedical Research Co., Ltd.

3. Experimental Method (1) Taking tumor from C57BL/6J mouse under aseptic condition, grinding and diluting it by physiological saline 1:3 (weight:volume), and giving hypodermic inoculation 0.2 ml per mouse in the armpit of the right forelimb of each mouse. dividing the mice into 7 groups randomly the next day, 10 in each group.

(2) After inoculation, waiting till the tumor has grown to the accessible size, administering medicine according to body weight, 0.5 ml/20 g intravenous, for 11 days, putting the mice to death on the $19^{th}$ after inoculation, taking out and weighing the tumor, and calculating the tumor inhibiting rate.

(3) dosage (mg/kg/d) and means of administration as shown in Table 3:

TABLE 3

Dosage (mg/kg/d) and means of administration:

| Group No. | Medication | Dosage | Number of animal | Sex | Administration plan |
|---|---|---|---|---|---|
| Group 1 | AS | 50 mg/kg | 10 | female | iv × 10 qd |
| Group 2 | AS | 100 mg/kg | 10 | female | iv × 10 qd |
| Group 3 | AS | 200 mg/kg | 10 | female | iv × 10 qd |
| Group 4 | DDP | 1 mg/kg | 10 | female | iv × 10 qd |
| Group 5 | AS + DDP | 50 mg/kg + 1 mg/kg | 10 | female | iv × 10 qd |
| Group 6 | CTX | 30 mg/kg | 10 | female | ip × 10 qd |
| Group 7 | NaCl | | 10 | female | iv × 10 qd |

(4) Judging the result with the following formula:

$$\text{Tumor inhibiting rate} = \frac{\text{Tumor weight of control group} - \text{tumor weight of administration group}}{\text{Tumor weight of control group}} \times 100\%$$

II. Experiment Result

During the experiment, no death occurred in any group. The experiment results of inhibiting Lewis lung cancer with AS administration as well as joint administration of AS and DDP are shown in Table 4.

TABLE 4

The experiment result for inhibiting tumor in mice bearing Lewis lung cancer by joint administration of AS and DDP

| Sample | Dosage mg/kg | Means of administration | Number of animal | Tumor weight (g) | Tumor inhibiting rate % |
|---|---|---|---|---|---|
| AS | 50 | i.v. | 5/5 | 3.03 ± 0.55 | 35.5% |
| AS | 100 | i.v. | 5/5 | 2.99 ± 0.50 | 36.4% |
| AS | 200 | i.v. | 5/5 | 2.25 ± 0.75 | 52.1% |
| DDP | 1 | i.v. | 5/5 | 2.52 ± 0.80 | 46.4% |
| AS + DDP | 50 ± 1 | i.v. | 5/5 | 2.13 ± 0.61 | 54.7% |
| CTX | 30 | i.p. | 5/5 | 1.68 ± 0.15 | 64.3% |
| Control | 0.9% NaCl | i.v. | 5/5 | 4.70 ± 0.46 | |

III. Result Analysis 3,4,5,4'-tetramethoxyl-α,β-diphenylethane-3'-O-sodium sulphate is quite effective in inhibiting the tumor in murine model of Lewis lung cancer, and its joint administration with DDP showed certain coordinated effect in inhibiting the tumors in murine model of Lewis lung cancer.

By directional targeting, 3,4,5,4'-tetramethoxyl-α,β-diphenylethane-3'-O-sodium sulphate pointedly affect tumor vessels, having tumor inhibiting effect on all solid tumors. There have been researches and reports on the adaptation diseases of Combretastatin A-4, medicine of the same kind. Therefore, changes can be made based on above experiments, and all the solid tumors applicable are within the scope of claims of this invention.

The above description of the embodiments of this invention does not limit this invention. Those skilled in the art can make various changes and transfigurations according to this invention, and such changes and modifications will be within the scope of the claims of this invention as long as they do not get away from the spirit of this invention.

What is claimed is:

1. A method for treating a tumor, wherein said method comprises administering to a subject in need thereof an effective amount of the compound of formula (I):

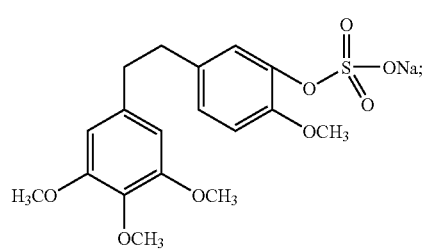

(I)

wherein said tumor is sarcoma or carcinoma.

2. The method of claim 1, wherein Na is replaced with H, K, NH₄, a substituted ammonium ion, or another metal or organic ion.

3. The method of claim 1, wherein said tumor is sarcoma.

4. The method of claim 1, wherein said tumor is lung cancer.

5. A method for treating a tumor, wherein said method comprises administering to a subject in need thereof an effective amount of the compound of formula (I) in combination with another antitumor therapy:

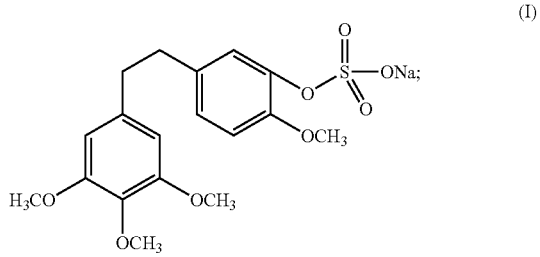

(I)

wherein said tumor is sarcoma or carcinoma.

6. The method of claim 5, wherein said another antitumor therapy is chemotherapy.

7. The method of claim 6, wherein said chemotherapy is performed by administering to the subject an effective amount of a chemotherapeutic agent selected from the group consisting of Cisplatin, fluorouracil, adriamycin, leuleran, melphalan, taxol, irinotecan, Avastin, N-acetylcochinol-O-phosphate, and anti-vascular endothelial cadherin antibody.

8. The method of claim 7, wherein said chemotherapeutic agent is Cisplatin.

9. The method of claim 1, wherein said tumor is carcinoma.

10. The method of claim 5, wherein said tumor is sarcoma.

11. The method of claim 5, wherein said tumor is carcinoma.

12. The method of claim 5, wherein said tumor is lung cancer.

13. The method of claim 5, wherein Na is replaced with H, K, NH₄, a substituted ammonium ion, or another metal or organic ion.

* * * * *

UNITED STATES PATENT AND TRADEMARK OFFICE
CERTIFICATE OF CORRECTION

PATENT NO. : 7,632,863 B2  Page 1 of 1
APPLICATION NO. : 12/023778
DATED : December 15, 2009
INVENTOR(S) : Yiping Li et al.

It is certified that error appears in the above-identified patent and that said Letters Patent is hereby corrected as shown below:

On the title page item (73) Assignee: to read "Zhe Jiang Cell Biomedical Research Co., Ltd."

Signed and Sealed this

Thirtieth Day of March, 2010

David J. Kappos
*Director of the United States Patent and Trademark Office*